(12) United States Patent
Kam (10) Patent No.: US 12,310,839 B2
(45) Date of Patent: May 27, 2025

(54) EXPANDING ANCHOR

(71) Applicant: CONMED CORPORATION, Utica, NY (US)

(72) Inventor: Andrew Kam, Odessa, FL (US)

(73) Assignee: CONMED CORPORATION, Utica, NY (US)

( * ) Notice: Subject to any disclaimer, the term of this patent is extended or adjusted under 35 U.S.C. 154(b) by 809 days.

(21) Appl. No.: 16/621,799

(22) PCT Filed: Jun. 11, 2018

(86) PCT No.: PCT/US2018/036838
§ 371 (c)(1),
(2) Date: Dec. 12, 2019

(87) PCT Pub. No.: WO2018/231681
PCT Pub. Date: Dec. 20, 2018

(65) Prior Publication Data
US 2020/0188087 A1  Jun. 18, 2020

Related U.S. Application Data (60) Provisional application No. 62/518,245, filed on Jun. 12, 2017.

(51) Int. Cl.
*A61F 2/08* (2006.01)

(52) U.S. Cl.
CPC ..... *A61F 2/0811* (2013.01); *A61F 2002/0835* (2013.01); *A61F 2002/0841* (2013.01);
(Continued)

(58) Field of Classification Search
CPC ............ A61F 2/0811; A61F 2002/0835; A61F 2002/0841; A61F 2002/0882;
(Continued)

(56) References Cited

U.S. PATENT DOCUMENTS 3,846,846 A * 11/1974 Fischer ................. A61F 2/3662
623/23.18
5,108,431 A 4/1992 Mansat et al.
(Continued)

FOREIGN PATENT DOCUMENTS

| CN | 102413777 | 4/2012 |
| EP | 1378202 | 1/2004 |
| FR | 2728779 | 7/1996 |

OTHER PUBLICATIONS

International Search Report Form PCT/ISA/220, International Application No. PCT/US2018/036838, pp. 1-15, dated Sep. 10, 2018.
(Continued)

*Primary Examiner* — Yashita Sharma (57) ABSTRACT

An anchoring system for a knee ligament reconstruction that can secure a graft within a bone tunnel. The anchor system includes an anchor having a tubular body extending along a longitudinal axis from a proximal end to a distal end. A conical head is fixed to the distal end of the tubular body. A series of expandable segments are positioned along the tubular body and moveable along the body into a compacted, deployed position where the segments expand radially to engage the inside of a bone tunnel. A threaded drive member may move the segments to the deployed configuration once the anchor and graft are positioned in the bone tunnel. A drive tool may be used to advance the drive member and can include a moveable shaft that pushes a strike plate out of the rear of the handle to provide an indication whether the anchor has been fully deployed.

13 Claims, 8 Drawing Sheets

(52) U.S. Cl.
CPC ............... *A61F 2002/0882* (2013.01); *A61F 2230/0067* (2013.01); *A61F 2250/001* (2013.01)

(58) Field of Classification Search
CPC ........ A61F 2230/0067; A61F 2250/001; A61F 2/0805; A61B 17/0401; A61B 2017/0464; A61B 2017/0409
See application file for complete search history.

(56) References Cited

U.S. PATENT DOCUMENTS

| | | |
|---|---|---|
| 9,724,140 B2 * | 8/2017 | McCormick ....... A61B 17/8891 |
| 9,795,428 B2 | 10/2017 | Levy et al. |
| 2005/0240222 A1 * | 10/2005 | Shipp .................. A61B 17/064 606/219 |
| 2009/0043342 A1 | 2/2009 | Freedland |

OTHER PUBLICATIONS

CN Office Action, Application No. 201880052176.8, pp. 1-8, dated May 7, 2021.

* cited by examiner

EXPANDING ANCHOR

CROSS-REFERENCE TO RELATED APPLICATIONS

The present application claims priority to U.S. Provisional No. 62/518,245, filed on Jun. 12, 2017.

BACKGROUND OF THE INVENTION

1. Field of the Invention

The present invention relates to knee ligament reconstruction and, more particularly, to an expanding anchor that can be used as an interference fixing device in a knee ligament reconstruction.

2. Description of the Related Art

During knee ligament reconstructions, such anterior cruciate ligament surgery, a soft tissue graft often needs to be pulled into and secured in a bone tunnel. Conventional approaches to anchoring the graft involve the use of an interference screw or anchor that is inserted into the bone tunnel after the graft is pulled into place. Although this approach provides a strong anchor point, insertion of the screw or anchor is difficult and associated with high failure rates. Accordingly, there is a need for an implant that can more readily be used to compress a graft against the walls of a bone tunnel for stabilization of the graft within the tunnel.

BRIEF SUMMARY OF THE INVENTION

The present invention provides an anchoring system for a knee ligament reconstruction that can secure a graft within a bone tunnel. In an embodiment, the anchor system comprises an anchor having a tubular body extending along a longitudinal axis from a proximal end to a distal end. A conical head is fixed to the distal end of the tubular body. A plurality of expandable segments are positioned along an intermediate portion of the tubular body and moveable between a un-deployed configuration, where the segments are spaced apart and radially contracted, and a deployed position, where the segments compacted together against the conical head and expanded radially. A first set of threads are disposed on an outer surface of the proximal end of the tubular body. A drive member may be positioned on the proximal end of the tubular body. The drive member may have a bore formed therethrough to define an inner surface and a distal portion of the inner surface includes a second set of threads that correspond to the first set of threads. Advancement of the drive member toward the conical head will move the plurality of segments from the un-deployed configuration to the deployed configuration. The conical head may include at least one scallop dimensioned to accept a tissue graft. The segments may be frustoconical and include at least one slot extending radially outward. A proximal portion of the inner surface of the drive member may include an inner non-circular geometry. The anchor system may further include a drive tool having a handle having a first end and second end, and a shank extending from the first end of the handle to a free end having an outer non-circular geometry that corresponds to the inner non-circular geometry of the drive member. The drive tool may further include a moveable shaft extending through the shank from the free end of the shank to the second end of the handle and a spring biasing the moveable shaft toward the free end of the shank. The drive tool may further include a strike plate coupled to the moveable shaft for movement between a first position, where the strike plate is received in the second end of the handle, and a second position, where the strike plate extends from the second end of the handle. Insertion of the free end of the shank into the drive member may align the proximal end of the tubular body with the moveable shaft of the drive tool such that any advancement of the drive tool along with the drive member along the tubular body in a first direction causes the tubular body to push the movable shaft in an opposite direction against the bias of the spring.

The present invention may additional comprise a method of securing a graft in a bone tunnel. A first step in the method is providing an anchor including a tubular body extending along a longitudinal axis from a proximal end to a distal end, a conical head fixed to the distal end of the tubular body, a plurality of expandable segments positioned along an intermediate portion of the tubular body, and a first set of threads disposed on an outer surface of the proximal end of the tubular body to the bone tunnel. A next step in the method involves placing the graft along the anchor so that the graft rests along the conical head and plurality of segments. A next step in the method involves positioning the anchor along with the graft into the bone tunnel. A next step in the method involves rotating a drive member having a second set of threads that correspond to the first set of threads about the tubular body to advance the drive member along the tubular body and compress the plurality of segments against the conical head so that the plurality of segments expand radially against the bone tunnel. The step of rotating the drive member may comprise inserting a shank of a drive tool having a non-circular outer geometry into a distal opening of the drive member having a corresponding non-circular inner geometry and turning the drive tool to correspondingly turn the drive member. The drive tool may have a moveable shaft that abuts a proximal end of the tubular body and is moved relative to the shaft as the drive tool advances the drive member to cause a strike plate to extend out of the handle.

BRIEF DESCRIPTION OF THE SEVERAL VIEWS OF THE DRAWING(S)

The present invention will be more fully understood and appreciated by reading the following Detailed Description in conjunction with the accompanying drawings, in which.

DETAILED DESCRIPTION OF THE INVENTION

Figure 1:
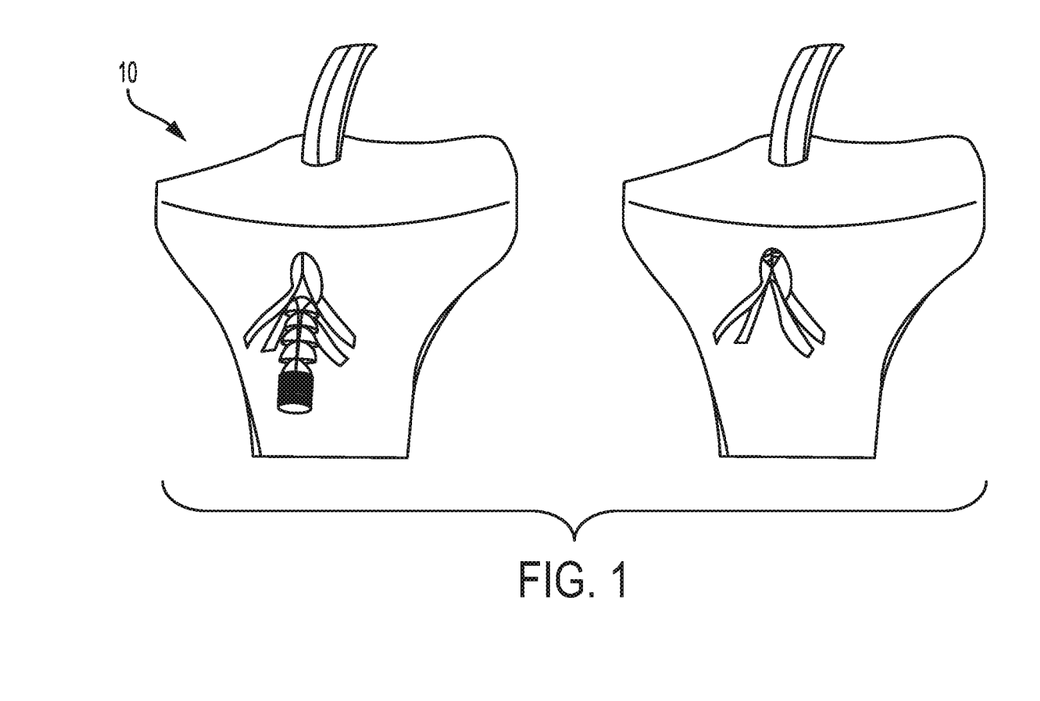
FIG. 1 is a schematic of an anchor according to the present invention inserted into a bone tunnel during a knee ligament reconstruction.
Figure 2:
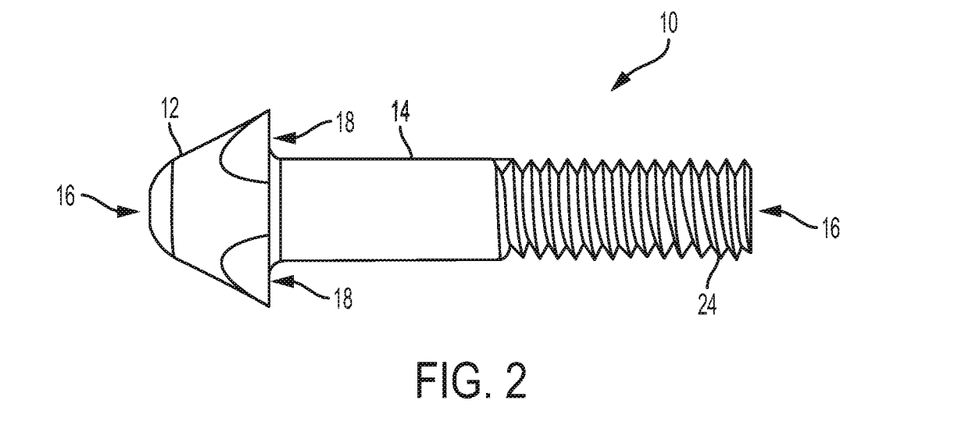
FIG. 2 is a side view of an anchor shaft and head according to the present invention.
Figure 3:
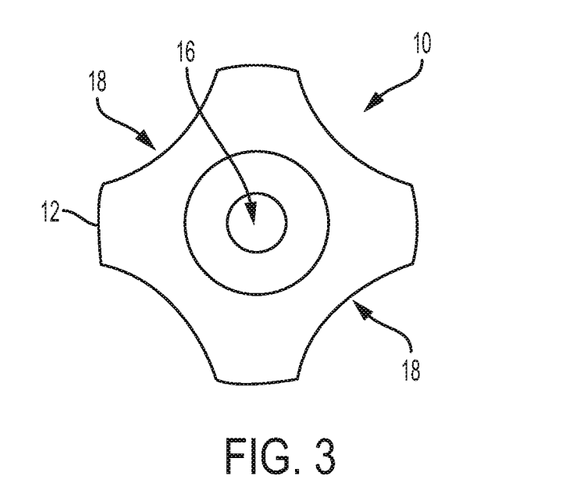
FIG. 3 is a front end view of an anchor shaft and head according to the present invention.

Referring to the figures, wherein like numeral refer to like parts throughout, there is seen in FIG. 1 an expanding anchor 10 according to the present invention for insertion into a bone tunnel during knee surgery and then deployment to retain a graft in the bone tunnel. Referring to FIGS. 2 and 3, anchor 10 comprises a head 12 that is generally conical fixed to a first end of a body 14 that is tubular. Body 14 is cannulated to have a through bore 16 to accept a guide wire or guide pin used to aid in placement of anchor 10 during a surgical operation. As seen in FIG. 3, head 12 may include one or more scallops 18 that can accommodate the limbs of a graft. The second end of body 14 includes exterior threads 24.

Figure 4:
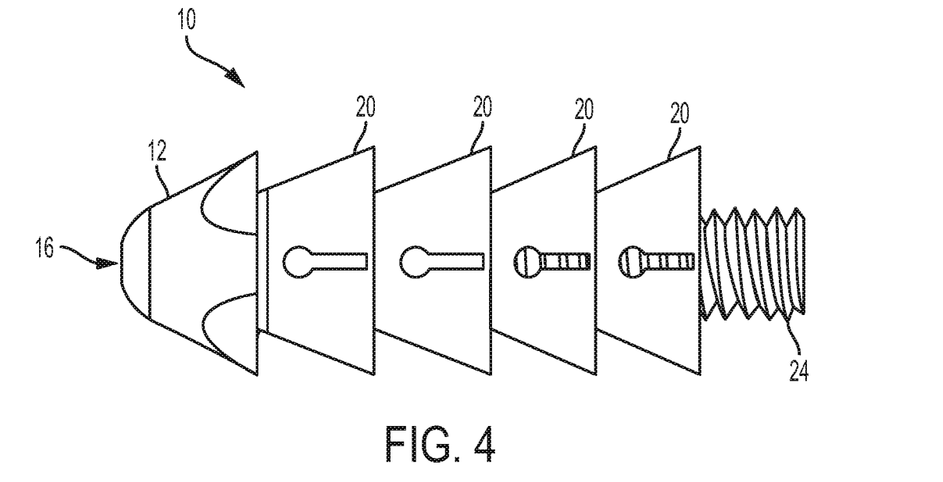
FIG. 4 is a side view of an anchor according to the present invention.
Figure 5:
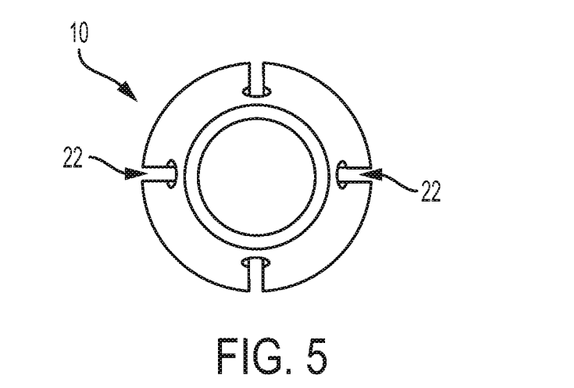
FIG. 5 is a front end view of an anchor according to the present invention.

Referring to FIG. 4, a series of segments 20 that are generally frustoconical are slidingly positioned along body 14 and oriented so that the taper of segments 20 expand outwardly toward a second end of body 14 opposite from head 12. Segments 20 are capable of movement between an un-deployed position, where segments 20 are spaced along tubular body 14 and have a smaller outer diameter, and a deployed position, where segments 20 are compressed together along body 14 toward head 12 to cause radial expansion of segments 20 to increase the radial diameter of segments 20. As seen in FIG. 5, segments 20 may include a series of radially extending slots 22 to promote radial expansion when compressed against head 12. While other geometries are possible, segments 20 must be capable of expanding sufficiently so that, when in the deployed position, segments 20 will secure anchor 10 within a bone tunnel and secure a graft positioned along the length of anchor 10 within a bone tunnel.

Figure 6:
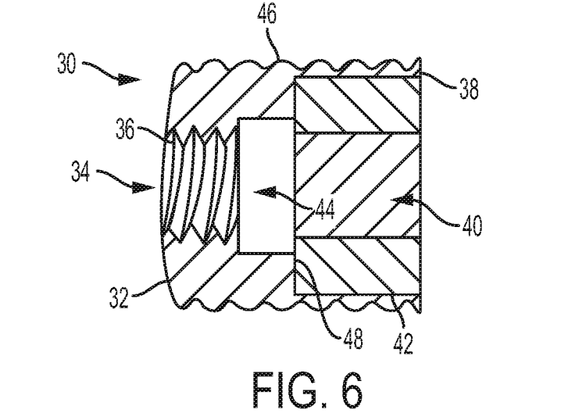
FIG. 6 is a cross-sectional view of a drive member according to the present invention.
Figure 7:
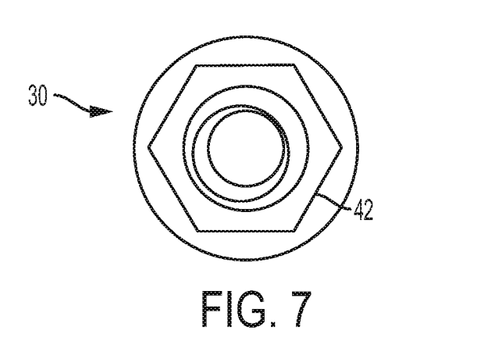
FIG. 7 is a front end view of a drive member according to the present invention.
Figure 8:
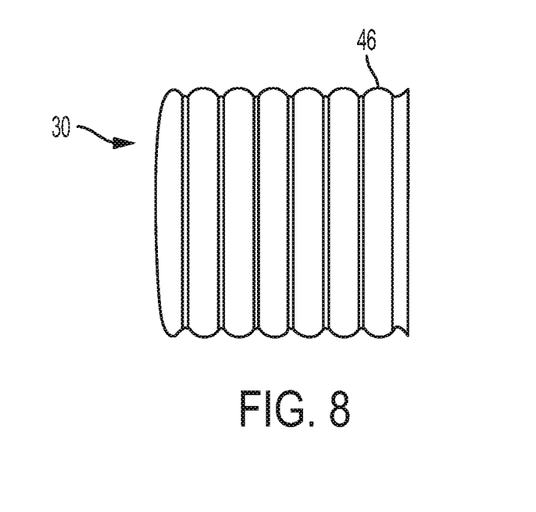
FIG. 8 is a side view of a drive member according to the present invention.
Figure 9:
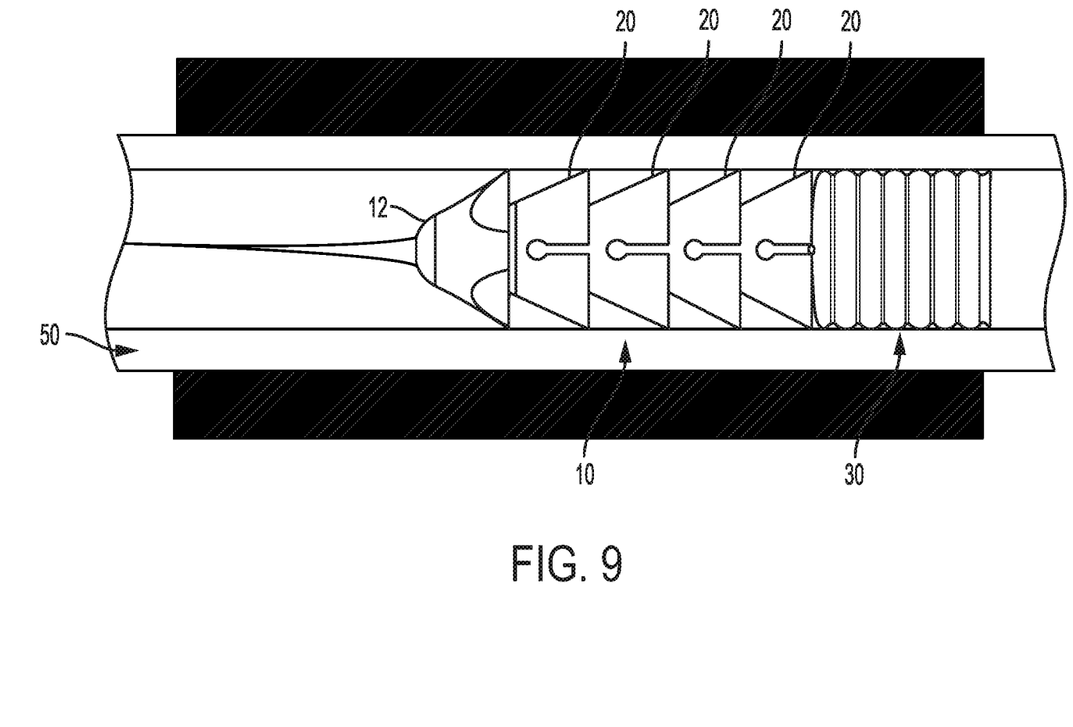
FIG. 9 is a cross-sectional view of an anchor according to the present invention positioned in a bone tunnel for a knee ligament reconstruction.
Figure 10:
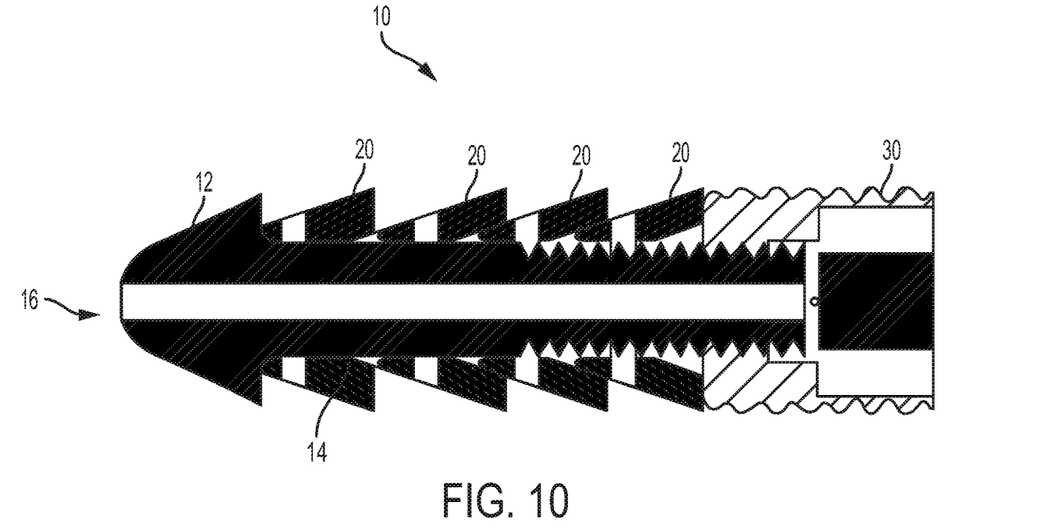
FIG. 10 is a cross-sectional view of an anchor according to the present invention prior to deployment.
Figure 11:
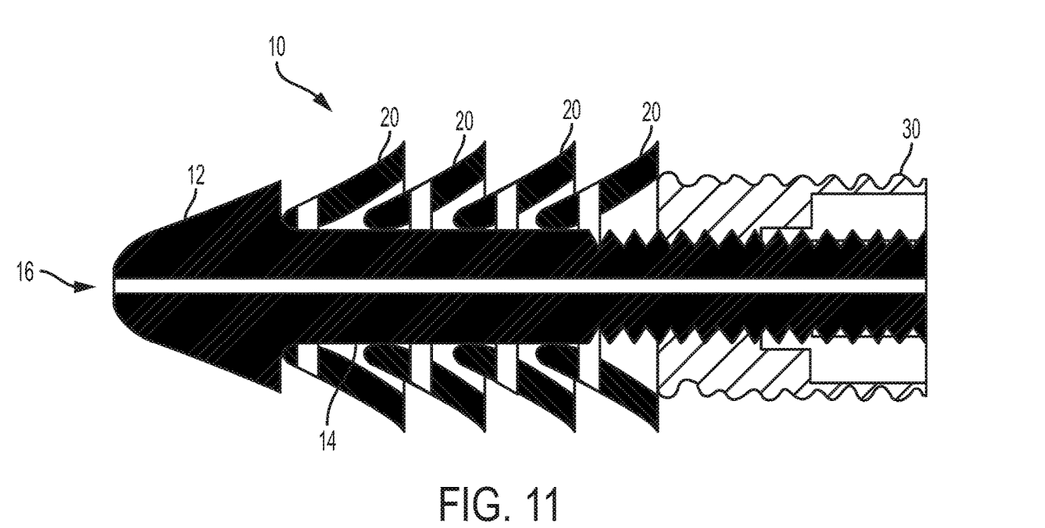
FIG. 11 is a cross-sectional view of an anchor according to the present invention after deployment.
Figure 12:
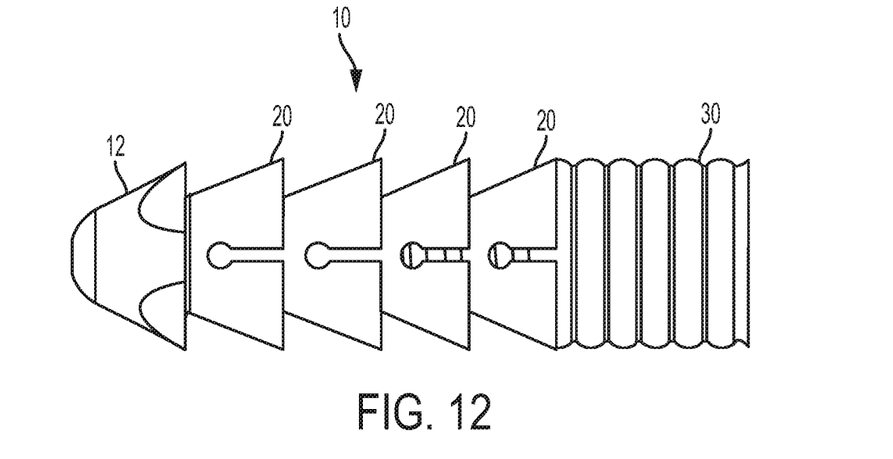
FIG. 12 is a side view of an anchor according to the present invention prior to deployment.
Figure 13:
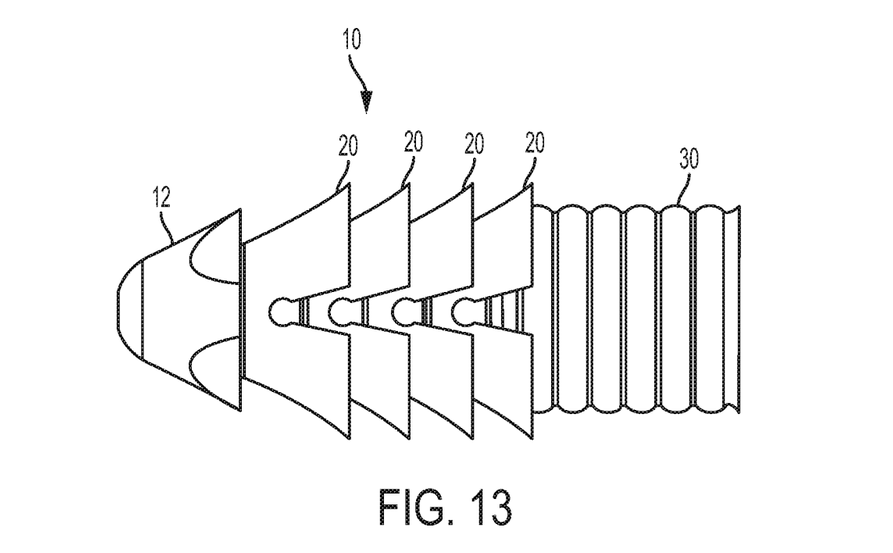
FIG. 13 is a side view of an anchor according to the present invention after deployment.

Referring to FIGS. 6 through 8, anchor 10 further includes a drive member 30 having a first end 32 with first cavity 34. First cavity 34 has a first internal diameter defining a set of internal threads 36 that correspond to the exterior threads 24 of body 14. Drive member 30 further includes a second end 38 having a second cavity 40 formed therein to define an internal surface 42 having a predetermined non-circular geometry, such as hexagonal, for coupling to and rotation by a correspondingly shaped tool, as described herein. Second cavity 40 includes passage 44 having a smaller internal diameter than second cavity 40 that extends to and is in communication with first cavity 34. A shoulder 48 is formed by the difference in internal dimension between passage 44 and second cavity 40. Drive member 30 may additionally include a series of exterior ribs 46 extending therearound. Drive member 30 may be positioned on body 14 and inserted into a bone tunnel 50 as seen in FIG. 9 for deployment. Referring to FIGS. 10 through 13, if drive member 30 is rotated by a tool interfaced with second cavity 40, drive member 30 will advance over body 14 from a first non-deployed position, as seen in FIGS. 10 and 12, to a second deployed positioned, as seen in FIGS. 11 and 13, where segments 20 are longitudinally compacted against head 12 so that the outer portions of segments 20 are expanded radially to engage the interior of bone tunnel 50 to lock anchor 10 and any graft associated therewith firmly in place.

Figure 14:
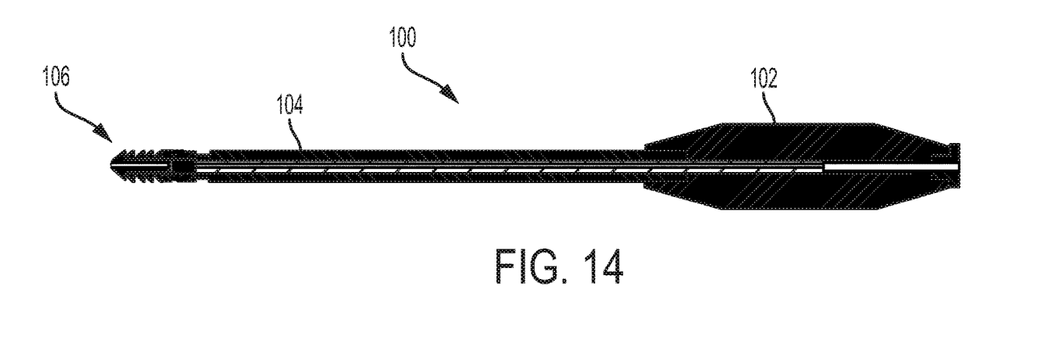
FIG. 14 is a cross-sectional view of a driver for an anchor according to the present invention.
Figure 15:
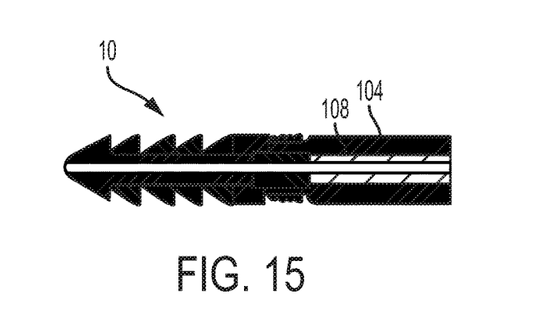
FIG. 15 is a cross-sectional view of an end of a driver for an anchor according to the present invention.
Figure 16:
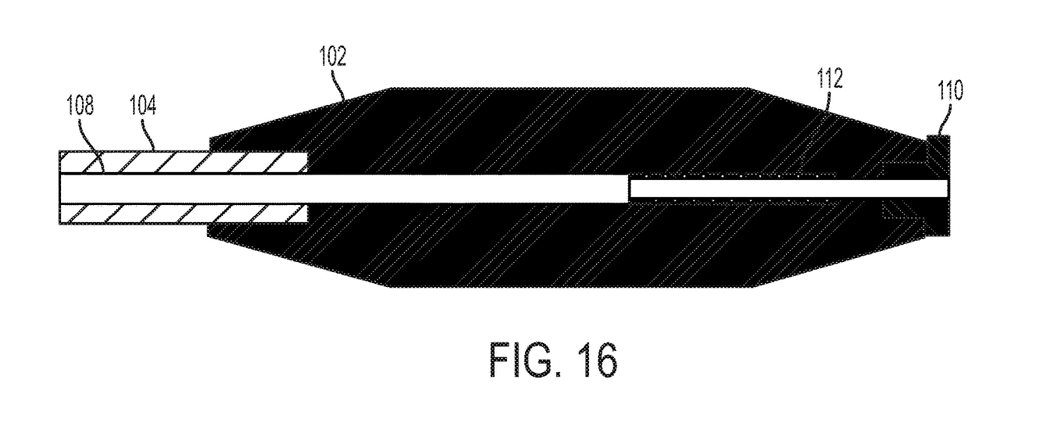
FIG. 16 is a cross-sectional view of a handle of a driver for an anchor according to the present invention.

Referring to FIGS. 14 through 16, the present invention may further comprise a driver 100 configured to aid in the insertion and deployment of anchor 10. Driver 100 includes a handle 102 and a shank 104 terminating in a first end 106 having a predetermined outer geometry that corresponds to internal surface 42 of second cavity 40 of drive member 30. Driver 100 additionally includes a moveable depth shaft 108 positioned internally of shank 104 and dimensioned to extend into drive member 30 into abutment with body 14 in passage 44 of drive member 30. Depth shaft 108 is biased toward first end 106 by a spring 112 mounted within handle 102. Depth shaft 108 extends through handle 102 into engagement with a strike plate 110 mounted in the opposite end of handle 102 from shank 104. Strike plate 110 is moveable between a first position, where strike plate 110 is flush with handle 102, and second position, where strike plate 110 extends from handle and provides a visible indication of the amount of movement of depth shaft 108.

It should be recognized that when driver 100 is positioned so that first end 106 is inside second cavity 40 of drive member 30 when drive member 30 is positioned on body 14, depth shaft 108 will extend to abut body 14 in passage 44. As drive member 30 is rotated to advance drive member 30 onto body 14, body 14 of anchor 10 will begin to extend through passage 44 and provide a longitudinal force against shaft 108 if first end 106 of driver 100 is maintained in second cavity 40 of drive member 30. The force applied longitudinally to shaft 108 within first end 106 by body 14 will compress spring 112 and thus cause strike plate 110 to extend from handle 102. As a result, the amount of movement of strike plate 110 out of handle 102 can provide an indication of how far first end 106 has moved relative to depth shaft 108, and thus how far drive member 30 has been advanced along body 14 of anchor 10. An indicator mark may thus be placed onto strike plate 110 to identify when deployment of drive member 30 over anchor is has been completed so that anchor 10 is secured in place within the bone tunnel along with any graft extending along anchor 10 and through scallops 18.

What is claimed is:

1. An anchor system, comprising:
a tubular body extending along a longitudinal axis from a proximal end to a distal end;
a conical head fixed to the distal end of the tubular body;
a plurality of expandable segments positioned along an intermediate portion of the tubular body and moveable between an un-deployed configuration, where the plurality of expandable segments are spaced apart and radially contracted, and a deployed configuration, where the plurality of expandable segments are configured to be compacted together against the conical head and expanded radially and where a distal leading end of at least one of the plurality of expandable segments is positioned within a proximal trailing end of another one of the plurality of expandable segments; and
a first set of threads disposed on an outer surface of the proximal end of the tubular body.

2. The anchor system of claim 1, further comprising a drive member positioned on the proximal end of the tubular body.

3. The anchor system of claim 2, wherein the drive member has a bore formed therethrough to define an inner surface and a distal portion of the inner surface includes a second set of threads that correspond to the first set of threads.

4. The anchor system of claim 3, wherein advancement of the drive member toward the conical head will move the plurality of expandable segments from the un-deployed configuration to the deployed configuration.

5. The anchor system of claim 4, wherein the conical head includes at least one scallop dimensioned to accept a tissue graft.

6. The anchor system of claim 5, wherein each of the plurality of expandable segments are frustoconical.

7. The anchor system of claim 6, wherein each of the plurality of expandable segments include at least one slot extending radially outward.

8. The anchor system of claim 7, wherein a proximal portion of the inner surface of the drive member includes an inner non-circular geometry.

9. The anchor system of claim 8, further comprising a drive tool having a handle having a first end and second end, and a shank extending from the first end of the handle to a free end having an outer non-circular geometry that corresponds to the inner non-circular geometry of the drive member.

10. The anchor system of claim 9, wherein the drive tool further includes a moveable shaft extending through the shank from the free end of the shank to the second end of the handle and a spring that provides a bias to the moveable shaft toward the free end of the shank.

11. The anchor system of claim 10, wherein the drive tool further includes a strike plate coupled to the moveable shaft for movement between a first position, where the strike plate is received in the second end of the handle, and a second position, where the strike plate extends from the second end of the handle.

12. The anchor system of claim 11, wherein insertion of the free end of the shank into the drive member aligns the proximal end of the tubular body with the moveable shaft of the drive tool such that any advancement of the drive tool along with the drive member along the tubular body in a first direction causes the tubular body to push the movable shaft in an opposite direction against the bias of the spring.

13. The anchor system of claim 1, wherein the at least one of the plurality of expandable segments includes at least one slot extending axially from the proximal trailing end towards the distal leading end thereof.

\* \* \* \* \*